United States Patent
Seydoux et al.

(10) Patent No.: US 6,936,165 B2
(45) Date of Patent: Aug. 30, 2005

(54) DEVICE FOR MOUNTING AN ELONGATE ELEMENT WITH AXIAL CLAMPING

(75) Inventors: Daniel Seydoux, Holtzheim (FR); Franck Muller, Strasbourg (FR)

(73) Assignee: Bio-Rad Pasteur (Societe Anonyme), Marnes la Coquette (FR)

( * ) Notice: Subject to any disclaimer, the term of this patent is extended or adjusted under 35 U.S.C. 154(b) by 98 days.

(21) Appl. No.: 10/477,898

(22) PCT Filed: Mar. 21, 2003

(86) PCT No.: PCT/FR03/00915

§ 371 (c)(1),
(2), (4) Date: Nov. 19, 2003

(87) PCT Pub. No.: WO03/081114

PCT Pub. Date: Oct. 2, 2003

(65) Prior Publication Data

US 2004/0144709 A1 Jul. 29, 2004

(30) Foreign Application Priority Data

Mar. 22, 2002 (FR) .......................... 02 03645

(51) Int. Cl.$^7$ .............................................. B01D 15/08
(52) U.S. Cl. .................... 210/198.2; 210/232; 210/656; 96/101; 285/320
(58) Field of Search ............................ 210/656, 198.2, 210/232; 96/101; 285/320, 332, 358, 394

(56) References Cited

U.S. PATENT DOCUMENTS

| 4,283,280 A | * | 8/1981 | Brownlee ................ 210/198.2 |
| 4,313,828 A | * | 2/1982 | Brownlee ................ 210/198.2 |
| 4,451,364 A | * | 5/1984 | Higgins et al. .......... 210/198.2 |
| RE31,974 E | * | 8/1985 | Brownlee ................ 210/198.2 |
| 4,604,198 A | * | 8/1986 | Dailey et al. ............ 210/198.2 |
| 5,472,598 A | * | 12/1995 | Schick .................... 210/198.2 |
| 5,482,628 A | * | 1/1996 | Schick .................... 210/198.2 |
| 5,985,140 A | * | 11/1999 | Dewaele ................. 210/198.2 |
| 6,090,190 A | * | 7/2000 | Enhsen et al. ............... 96/101 |

* cited by examiner

Primary Examiner—Ernest G. Therkorn
(74) Attorney, Agent, or Firm—Young & Thompson

(57) ABSTRACT

Device for mounting an elongated element with axial clamping, includes a body forming a support base whereon are fixed a stop part including a first support element for one end of the elongated element and a retaining part, the parts being axially separated, a removable support block comprising a through passage for receiving the elongated element and capable of being wedged between the retaining part and stop part, and a mobile part including a second support element for the other end of the elongated element, the mobile part is secured in articulation to two link rods mounted at their opposite ends, potentially rotatable, on two eccentrics mounted potentially rotatable on the body and rigidly assembled to a pivoting cover provided with a member or zone for gripping or maneuvering, the cover or lid substantially covering the assembly of the parts and the elements when it is folded down.

15 Claims, 5 Drawing Sheets

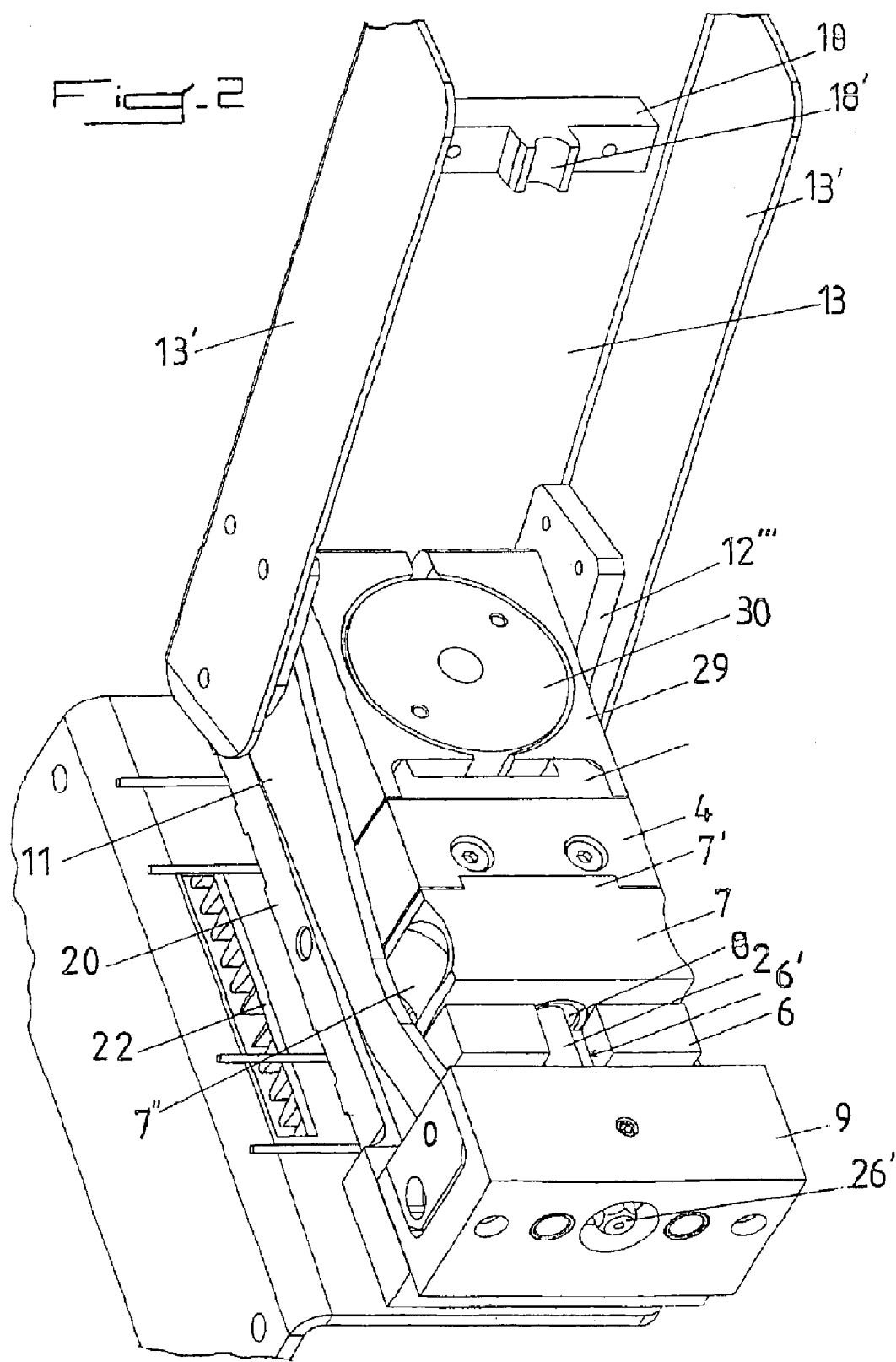

DEVICE FOR MOUNTING AN ELONGATE ELEMENT WITH AXIAL CLAMPING

REFERENCE TO RELATED APPLICATIONS

This application is a 371 of PCT/FR03/00915 filed Mar. 21, 2003.

The present invention relates to systems and devices intended to support, temporarily and under stress, elongate elements such as, for example, cartridge holders for gel cartridges used in combination with high-pressure chromatographs and concerns a device for mounting an elongate element and a corresponding cartridge holder.

There are numerous applications in which it is necessary frequently to mount/dismount an interchangeable element in a system, while at the same time ensuring precise positioning, possibly under stress, of said element when mounted.

However, present-day devices for fulfilling these functions have a relatively complex, bulky structure and are awkward to handle.

A particular embodiment of the aforementioned type is to be found in high-pressure chromatographs and, more precisely, in relation to cartridge holders pertaining to chromatographs of this type.

Present-day cartridge holders, as disclosed, in particular, by documents U.S. Pat. No. 5,472,598 and U.S. Pat. No. 5,482,628, do not allow rapid mounting/dismounting (constituent parts assembled by screwing), require the availability of free access from all directions, and do not allow optimal sealing to be ensured after each mounting, nor, if necessary, smooth heat regulation.

The object of the present invention is, in particular, to propose a solution which allows at least some of the aforementioned drawbacks to be overcome.

For this purpose, the invention relates to a device for mounting an elongate element with axial gripping and precise alignment, in particular a removable tubular element to be integrated in a sealed manner into a circulation circuit passing through said device, characterised in that it mainly consists, on the one hand, of a rigid body defining an axial direction and forming a base on which a stop part, comprising a first support element for one of the ends of the elongate element, and a part for at least partial holding of said elongate element are formed or fixed, these parts being axially separated, and, on the other hand, of a removable support block comprising a through-passage to receive in a fitted but sliding manner at least one portion of the elongate element and capable of being positioned with chocks between the holding part and the stop part by entering into surface contact with at least the stop part, and, finally, of a moving part guided in the direction and comprising a second support element for the other end of the elongate element, said moving part being connected to or integral with means transforming the pivoting movement of a handling device into a translational movement in said axial direction of said moving part.

A better understanding of the invention will be facilitated by the following description, which relates to a preferred embodiment, given by way of a non-limiting example and explained with reference to the accompanying schematic drawings, in which:

BRIEF DESCRIPTION OF THE DRAWINGS

FIG. 2 is a perspective view of the device of FIG. 1, the elongate element being in place and the lid being in the raised position (absence of gripping of the elongate element);

DESCRIPTION OF THE PREFERRED EMBODIMENTS

Figure 1:
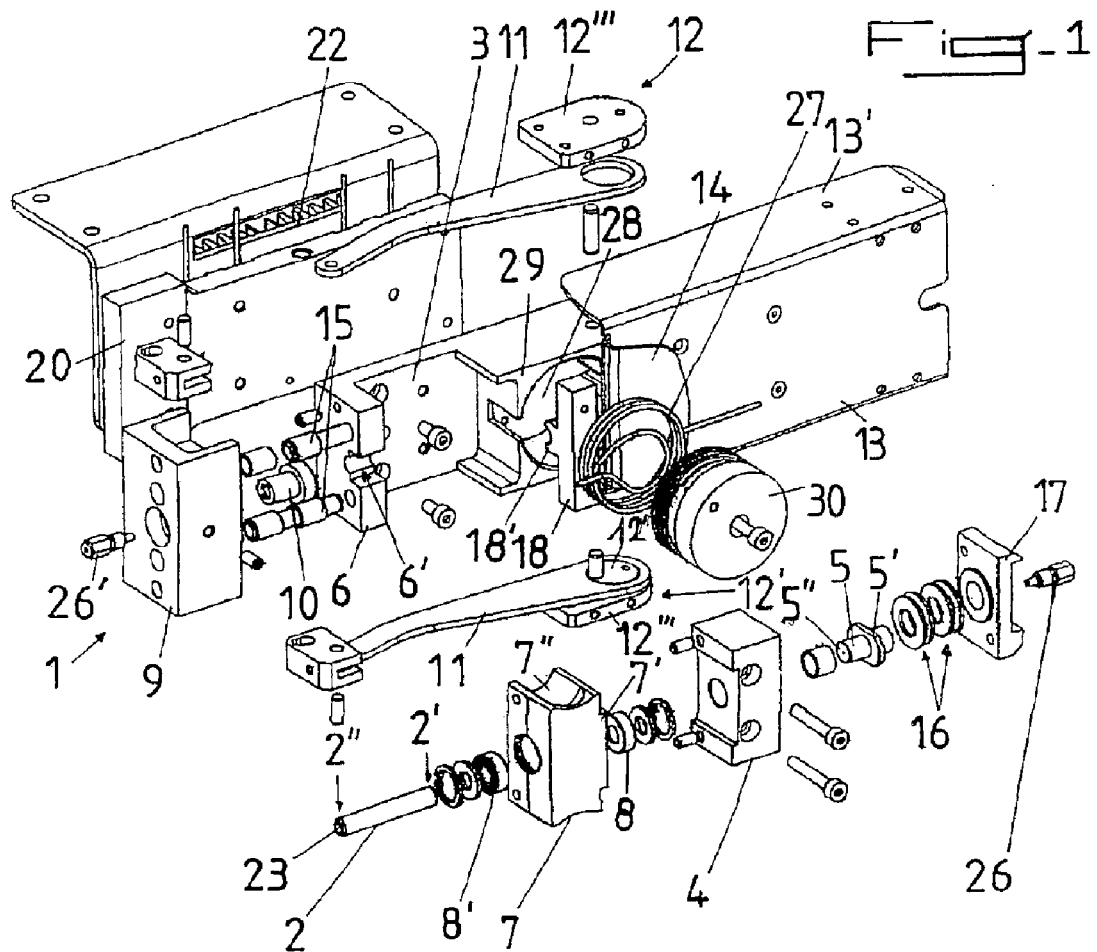
FIG. 1 is an exploded perspective view of a device according to the invention forming a cartridge holder.
Figure 6:
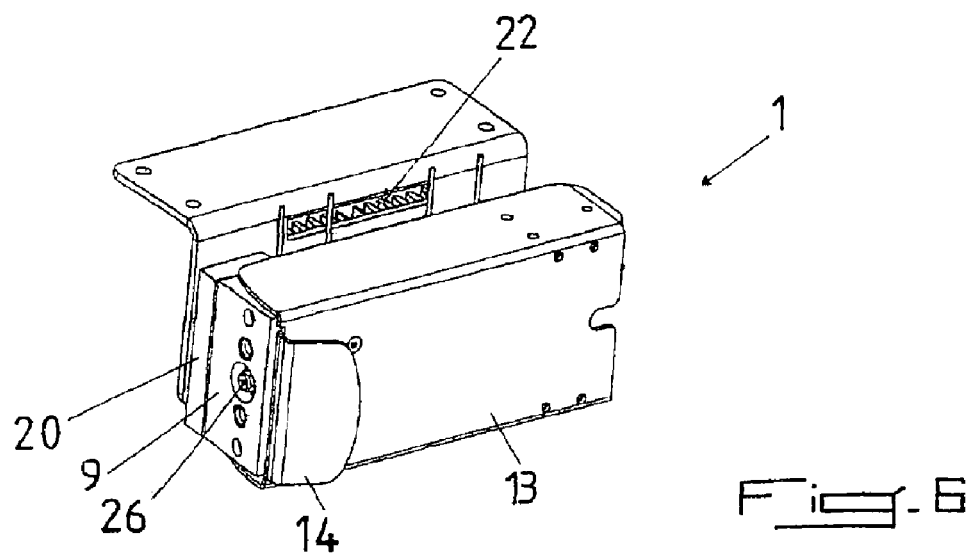
FIG. 6 is a perspective view of the device shown in FIG. 1, the lid being in the closed position.

As the figures of the accompanying drawings show, the invention relates to a device 1 for mounting an elongate element 2 with axial gripping and precise alignment, in particular a removable tubular element to be integrated in a sealed manner into a circulation circuit passing through said device 1.

This device 1 mainly consists, on the one hand, of an elongate rigid body 3 defining an axial direction X and forming a base on which a stop part 4, comprising a first support element 5 for one 2' of the longitudinal ends of the elongate element 2, and a part 6 for at least partial holding of said elongate element 2 are formed or fixed, these parts 4 and 6 being axially separated or mutually staggered, and, on the other hand, of a removable support block 7 comprising a through-passage 8 to receive in a fitted but sliding manner, or with a faculty for sliding, at least one portion of the elongate element 2 and capable of being positioned with chocks between the holding part 6 and the stop part 4 by entering into surface contact with at least the stop part, and, finally, of a moving part 9 guided in translation in the direction X and comprising a second support element 10 for the other end 2" of the elongate element 2, said moving part 9 being integral with means 11, 11'; 12, 12' transforming the pivoting movement of a handling device 13, 14 into a translational movement of said moving part 9 in said direction X.

According to an advantageous embodiment of the invention shown in the accompanying drawings, the moving part 9 is attached, in an articulated manner, to two connecting pieces 11, 11' mounted, at their ends remote from said moving part 9, in a rotatable manner, on respective cams 12, 12' attached in a rotatable manner to the body 3 forming a base and rigidly assembled with a part 13 forming a pivoting lever provided with a gripping member or zone 14, the two assemblies of cams 12, 12'/connecting pieces 11, 11' transforming the pivoting movement of the lever 13 into a translational movement of the moving part 9.

The lever 13 may, for example, consist of a mere handle which can be displaced by pivoting between a raised position (part 9 released) and a closed position against the parts 4, 6, 9 (part 9 engaged and gripped).

Preferably, however, the single handling device will consist of a cap or lid 13 forming a pivoting lever and provided with a terminal gripping device or zone 14 for displacing said lever, said lid or cap 13 covering substantially all of the parts 4, 6, 9 and the elements 5, 7, 10 in its closed position, corresponding to the gripped state of the elongate element 2, thus forming at least partially, in cooperation with the base 3, a basic protective and heat insulating chamber surrounding the aforementioned components.

The course of the moving part 9 will, of course, be defined in such a way that, when the lid 13 is closed, the elongate element 2 is gripped with at least a minimal predetermined force between the first and the second support elements 5 and 10, and that, when the lid 13 is raised, said elongate element 2 is entirely disengaged and may easily be removed from the device 1 with the support block 7 in which it is arranged.

The elongate element 2 can thus be gripped and released by mere limited pivoting movements of the lid 13, the handling and precise positioning of said elongate element 2 are facilitated by virtue of its combination with the support block 7, and limited force is required for the mounting with gripping.

Each cam 12, 12' comprises a discoid part 12", around which the corresponding connecting piece 11, 11' is freely rotatably mounted, and a part 12''' linked to the lid 13, a cylindrical rod portion connecting it rotatably to the body 3.

A possible articulated connection of the connecting pieces 11, 11' in the region of the moving part 9 is shown by way of an embodiment in the figures of the accompanying drawings.

Figure 3:
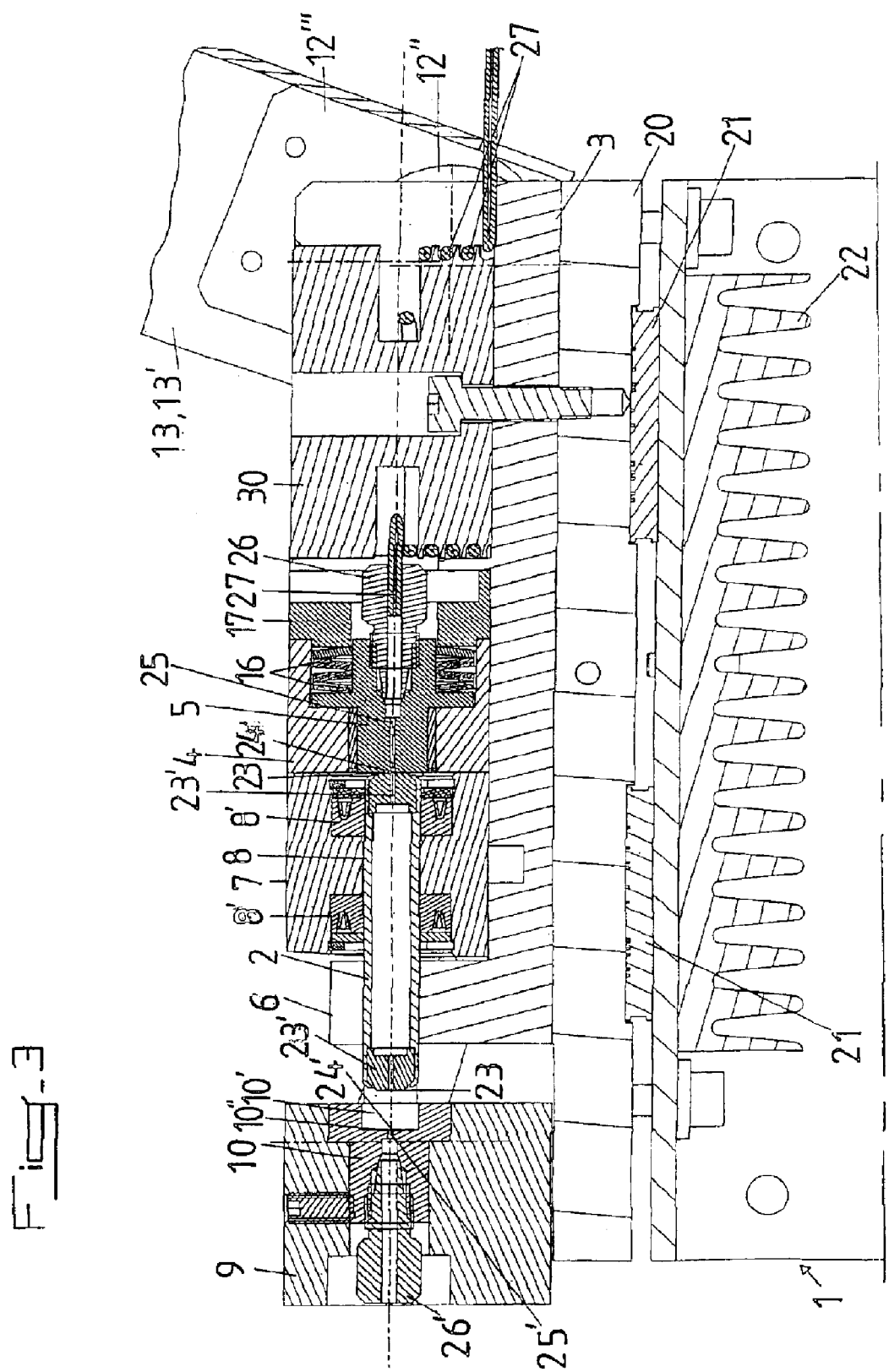
FIG. 3 is a cross-section in a vertical plane comprising the longitudinal axis of the elongate element of the device of FIG. 2.
Figure 4:
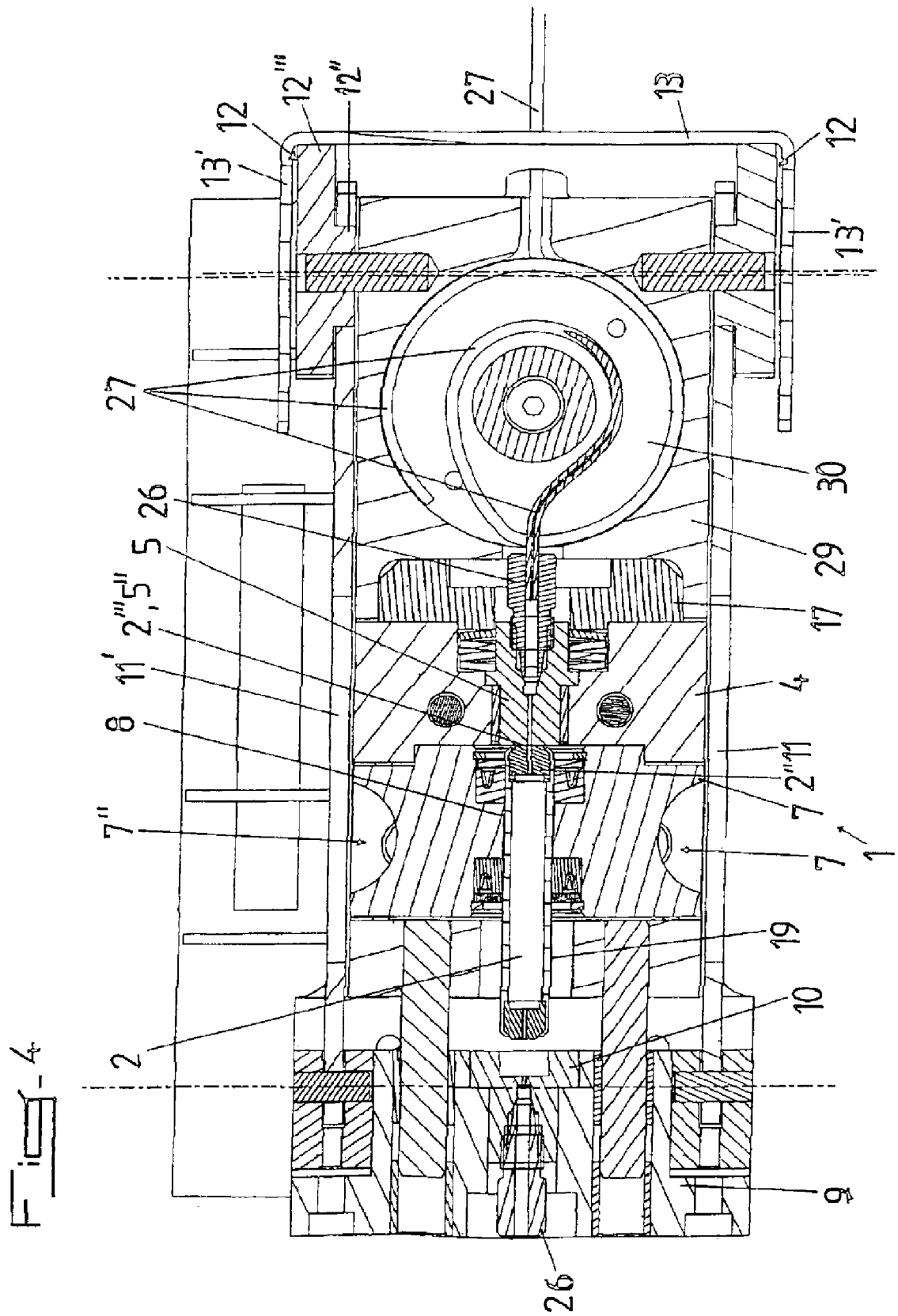
FIG. 4 is a cross-section in a horizontal plane passing through the longitudinal axis of the elongate element of the device of FIG. 2.
Figure 5:
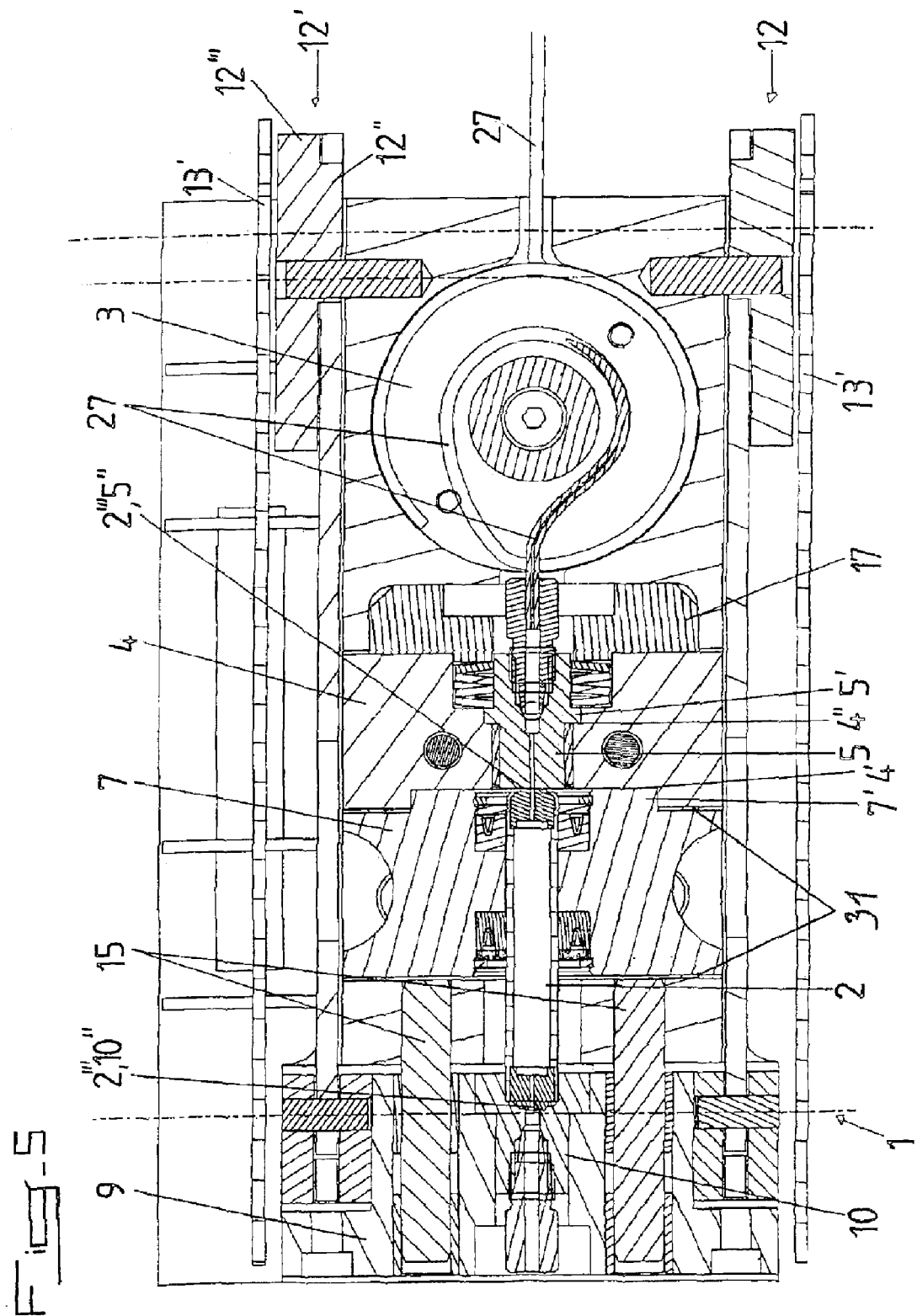
FIG. 5 is a cross-section similar to that of FIG. 4, the lid being in the closed position and the elongate element being subjected to axial gripping.

According to a first characteristic of the invention, shown, in particular, in FIGS. 3 to 5 of the accompanying drawings, the support block 7 comprises, in the region of its face intended to be turned towards the stop part 4, at least one protruding part 7' in the form of a profiled rib cooperating in a mating manner with at least one recess in the form of a profiled groove 41, made in the face facing the stop part 4, allowing said block 7 to be slid in a guided manner between the holding part 6 and the stop part 4, perpendicularly to the plane of the body 3 and to the direction X, and said block 7 to be held laterally when mounted.

Preferably, the rib 7' and the groove 4' will have a rectangular or dovetail contour in section.

In order to hold the elongate element 2 precisely in the support block 7 with resilient gripping, while allowing easy mounting/dismounting with respect thereto, the receiving passage 8 of the support block 7 is formed in part, at each of its ends, by a packing 8' gripping the elongate element 2 in an elastic manner.

To facilitate handling, and in particular removal, of the support block 7, the support block may have on its two exterior lateral faces, located either side of the axial direction X, cavities 7''' forming opposed gripping recesses for fingers, allowing said block 7 to be grasped firmly by pinching between these recesses.

In order to maintain precise positioning of the elongate element 2 during gripping and to be able to apply gripping forces in the axis of said elongate element 2, the second support element 10 of the moving part 9 comprises a hollow receiving site 10' for housing the end portion 2''' of the elongate element 2, protruding from the holding part 6 when the support block 7 is in the mounted position, and said moving part 9 is guided axially by at least two guiding rods 15, mounted in said moving part 9 and said holding part 6 in a fixed manner in one and in a sliding manner in the other.

In order to avoid damaging the elongate element 2 and to ensure that the gripping is of a preset intensity, the first support element 5 is mounted in the stop part 4 with a faculty for sliding in the axial direction X due to the thrust of the elongate element 2 when it is gripped axially, this taking place against an elastic action urging said first support element 5 against an internal stop 4" of said part 4 in the opposite direction along said axial direction X.

According to a preferred embodiment of the invention, shown, in particular, in FIGS. 1 and 3 to 5 of the accompanying drawings, the elastic action is provided by one or more pairs of spring washers 16, for example of the Belleville type, assembled head to tail in pairs, mounted under stress between a shoulder 5' of the first support element 5 and a part 17 forming a counter-stop, integral with the stop part 4 and/or the body 3 forming a base.

Furthermore, the parts 4 and 6 may optionally comprise, in the region of their surfaces intended to come into contact with the adjacent surfaces of the part 7, resilient elements of low height 31, such as blocks, which are entirely flattened when the lid 13 is shut in the closed position.

According to a further characteristic of the invention, allowing radial holding of the portion of the elongate element 2 protruding from the support block 7, as well as precise and reproducible definition of the closed position of the lid 13, the holding part 6 comprises a notch 6' in its upper portion, defining a portion of a receiving passage 19 for a portion of the elongate element 2, and the lid 13 comprises on its interior face, turned towards the parts 4, 6, 9 and the elements 5, 7, 10 that are covered when it is closed, a part 18 forming a stop, resting on the holding part 6 when the lid 13 is in the closed position, and provided with a protuberance 18' having a shape that is complementary to that of the notch 6' of the holding part 6, and forming the complementary portion of the receiving passage 19 for a portion of the elongate element 2 when said lid 13 is in the closed position (FIGS. 2 and 3).

According to a preferred embodiment of the invention, the lid 13 has a profiled structure with a U-shaped cross-section, the lateral wings 13' of which carry the cams 12, 12' and cover when said lid 13 is in the closed position, both the upper face and the lateral faces of the parts 4, 6, 9 and the elements 5, 7, 10, as well as the connecting pieces 11, 11' and optionally the body 3 forming a base.

When the lid 13 is in the closed position, therefore, the device 1 will form a substantially closed case, the functional components of which are inaccessible and protected from the outside. The provision of packings will allow the insulation of the internal volume thus delimited to be increased if necessary.

In order to facilitate operation of the lid 13 and to limit the force required when it is forced shut and grips the elongate element 2, the lid 13 is provided, in the region of its end remote from the cams 11, 11', with a gripping device 14 in the form of a handle, for example as a curved portion extending said end of said lid 13.

Advantageously, as shown in the figures of the accompanying drawings, the body forming a base 3, the holding parts 6 and stop parts 4, the support block 7 and the moving part 9 have solid structures made from a non-oxidising metal, such as, for example, stainless steel, and substantially parallelepiped shapes with flat opposing faces or surfaces in contact and sections which are substantially identical in planes perpendicular to the axial direction X.

These arrangements lead to a device 1 that is compact, easy to produce, resistant to deformation and rigid.

The holding part 6 may, for example, be formed as a single piece with the body 3, and the stop part 4 be attached to the body 3 by screwing or bolting.

According to an alternative embodiment for producing a temperature-regulated device 1, it may be provided that the body 3 forming a base is attached, with close surface contact, to a plate 20 forming a bed, carrying on its opposite face at least one Pelletier-effect element 21 associated with a radiator 22.

In certain applications, it may be necessary to be able to convey a fluid under high pressure through the elongate element 2, provided, at each of its ends 2', 2", in the region of its contact surfaces 2"' placed closely on corresponding contact surfaces 5"', 10"' of the first and second support elements 5, 10, with an orifice 23 opening from a corresponding circulation passage 23' for a fluid passing through said elongate element 2.

It may then be provided that said contact surfaces 5"', 10"' of said first and second support elements 5 and 10 are also each provided with an orifice 24, 24' opening from corresponding fluid-circulation passages 25, 25' made in these elements, the two juxtaposed orifices of each facing pair of orifices 23 and 24; 23 and 24' being, once the elongate element 2 has been gripped, in communication and aligned, the respective contact surfaces in close application against one another 2"' and 5"'; 2"' and 10"' forming a seal around said contiguous orifices 23 and 24; 23 and 24', the passages 25, 25' made in said support element 5 and 10 being connected to connecting and joining means 26, 26' for conduits 27, mounted on said elements 5 and 10 remote from their respective opening orifices 24 and 24'.

The present invention also relates to a cartridge holder for a high-pressure chromatograph, intended to support interchangeable cartridges which are generally filled with gel and permeated by the flow of liquid to be analysed, characterised in that it consists of a device 1 as described above, the elongate element 2 being formed from a cylindrical cartridge of the aforementioned type.

According to an advantageous supplementary characteristic of the invention, shown in the figures of the accompanying drawings, the support body forming a base 3 comprises a site 28, preferably surrounded by a circumferential lateral wall 29, and forming, with the pivoting lid 13 in the closed portion, a substantially closed volume to receive a drum 30, intended to support a plurality of turns of a liquid supply conduit 27, connected to the joining means 26 of the first support element 5, said drum 30 having a solid cylindrical structure made from a thermally conductive material and being fixed, via its base, with close surface contact, to said body forming a base 3.

This conduit coil 27 thus forms a thermally regulated fluid reservoir, allowing fluid to circulate at a practically constant temperature through the elongate element 2.

The site 28 may optionally be cut in the block of material forming the body 3.

The invention is not, of course, limited to the embodiment described and illustrated in the accompanying drawings. Modifications are possible, in particular with regard to the constitution of the various elements or by substitution of technical equivalents, without thereby departing from the scope of protection of the invention.

What is claimed is:

1. Device for mounting an elongate element with axial gripping and precise alignment, in particular a removable tubular element to be integrated in a sealed manner into a circulation circuit passing through said device, comprising a rigid body (3) defining an axial direction (X) and forming a base on which a stop part (4), comprising a first support element (5) for one (2') of the ends of the elongate element (2), and a part (6) for at least partial holding of said elongate element (2) are formed or fixed, these parts (4 and 6) being axially separated, a removable support block (7) comprising a through-passage to receive (8) in a fitted, but sliding, manner at least one portion of the elongate element (2) and capable of being positioned with chocks between the holding part (6) and the stop part (4) by entering into surface contact with at least the stop part (4), and, a moving part (9) guided in the direction (X) and comprising a second support element (10) for the other end (2") of the elongate element (2), said moving part (9) being connected to or integral with means (11, 11'; 12, 12') transforming the pivoting movement of a handling device (13, 14) into a translational movement in said direction (X) of said moving part (9).

2. Device according to claim 1, wherein the moving part (9) is attached, in an articulated manner, to two connecting pieces (11, 11') mounted, at their ends remote from said moving part (9), in a rotatable manner, on respective cams (12, 12') attached in a rotatable manner to the body (3) forming a base and rigidly assembled with a part (13) forming a pivoting lever provided with a gripping member or zone (14), the two assemblies of cams (12, 12')/connecting pieces (11, 11') transforming the pivoting movement of the lever (13) into a translational movement of the moving part (9).

3. Device according to claim 1, wherein the single handling device consists of a cap or lid (13) forming a pivoting lever and provided with a terminal gripping device or zone (14) for displacing said lever, said lid or cap (13) covering substantially all of the parts (4, 6, 9) and the elements (5, 7, 10) in its closed position, corresponding to the gripped state of the elongate element (2).

4. Device according to claim 3, wherein the lid (13) has a profiled structure with a U-shaped cross-section, the lateral wings (13') of which carry the cams (12, 12') and cover, when said lid (13) is in the closed position, both the upper face and the lateral faces of the parts (4, 6, 9) and the elements (5, 7, 10), as well as the connecting pieces (11, 11') and optionally the body (3) forming a base, and in that said lid (13) is provided, in the region of its end remote from the cams (11, 11'), with a gripping device (14) in the form of a handle.

5. Device according to claim 1, wherein the support block (7) comprises, in the region of its face intended to be turned towards the stop part (4), at least one protruding part (7') in the form of a profiled rib cooperating in a mating manner with at least one recess in the form of a profiled groove (4'), made in the face facing the stop part (4), allowing said block (7) to be slid in a guided manner between the holding part (6) and the stop part (4), perpendicularly to the plane of the body (3) and to the direction (X), and said block (7) to be held laterally when mounted.

6. Device according to claim 1, wherein the receiving passage (8) of the support block (7) is formed in part, at each of its ends, by a packing (8') gripping the elongate element (2) in an elastic manner, and in that said support block (7) has on its two exterior lateral faces, located either side of the axial direction (X), cavities (7") forming opposed gripping recesses for fingers.

7. Device according to claim 1, wherein the second support element (10) of the moving part (9) comprises a hollow receiving site (10') for housing the end portion (2") of the elongate element (2) protruding from the holding part (6) when the support block (7) is in the mounted position, and in that said moving part (9) is guided axially by at least two guiding rods (15), mounted in said moving part (9) and said holding part (6) in a fixed manner in one and in a sliding manner in the other.

8. Device according to claim 1, wherein the first support element (5) is mounted in the stop part (4) with a faculty for sliding in the axial direction (X) due to the thrust of the elongate element (2) when it is gripped axially, this occurring against an elastic action urging said first support element (5) against an internal stop (4") of said part (4) in the opposite direction along said axial direction (X).

9. Device according to claim 8, wherein the elastic action is provided by one or more pairs of spring washers (16), for example of the Belleville type, assembled head to tail in pairs, mounted under stress between a shoulder (5') of the first support element (5) and a part (17) forming a counter-stop, integral with the stop part (4) and/or the body (3) forming a base.

10. Device according to claim 1, wherein the holding part (6) comprises a notch (6') in its upper portion, defining a portion of a receiving passage (19) for a portion of the elongate element (2), and in that the lid (13) comprises on its interior face, turned towards the parts (4, 6, 9) and the elements (5, 7, 10) that are covered when it is closed, a part (18) forming a stop, resting on the holding part (6) when it is closed in the direction of the base (3) of the device (13, 19), and provided with a protuberance (18') having a shape that is complementary to that of the notch (6') of the holding part (6), and forming the complementary portion of the receiving passage (19) for a portion of the elongate element (2) when said device (13) is in the closed position.

11. Device according to claim 1, wherein the body (3) forming a base is attached, with close surface contact, to a plate (20) forming a bed, carrying on its opposite face at least one Pelletier-effect element (21) associated with a radiator (22).

12. Device according to claim 1, wherein the elongate element (2) is provided, at each of its ends (2', 2"), in the region of its contact surfaces (2") placed closely onto corresponding contact surfaces (5", 10") of the first and second support elements (5, 10), with an orifice (23) opening from a corresponding circulation passage (23') for a fluid, and in that said contact surfaces (5", 10") of said first and second support elements (5 and 10) are also each provided with an orifice (24, 24') opening from corresponding fluid-circulation passages (25, 25') made in these elements, the two juxtaposed orifices of each facing pair of orifices (23 and 24; 23 and 24') being, once the elongate element (2) has been gripped, in communication and aligned, the respective contact surfaces in close application against one another (2''' and 5"; 2''' and 10") forming a seal around said contiguous orifices (23 and 24; 23 and 24'), the passages (25, 25') made in said support element (5 and 10) being connected to connecting and joining means (26, 26') for conduits (27), mounted on said elements (5 and 10) remote from their respective opening orifices (24 and 24').

13. Device according to claim 1, wherein the body forming a base (3), the holding part (6) and stop part (4), the support block (7) and the moving part (9) have solid structures made from a non-oxidising metal, such as, for example, stainless steel, and substantially parallelepiped shapes with flat opposing faces or surfaces in contact and sections which are substantially identical in planes perpendicular to the axial direction (X).

14. Cartridge holder for a high-pressure chromatograph, intended to support interchangeable cartridges which are generally filled with gel and crossed by the flow of liquid to be analysed, wherein it consists of a device (1) according to claim 1, the elongate element (2) being formed from a cylindrical cartridge of the aforementioned type.

15. Cartridge holder according to claim 14, wherein the support body forming a base (3) comprises a site (28), preferably surrounded by a circumferential lateral wall (29), and forming, when the pivoting lid (13) is in the closed position, a substantially closed volume to receive a drum (30), intended to support a plurality of turns of a liquid supply conduit (27), connected to the joining means (26) of the first support element (5), said drum (30) having a solid cylindrical structure made from a thermally conductive material and being fixed, via its base, with close surface contact, on said body forming a base (3).

* * * * *